United States Patent [19]

Metzner et al.

[11] Patent Number: 5,248,450
[45] Date of Patent: Sep. 28, 1993

[54] COMPOSITION FOR USE AN AN AGENT OR CONCENTRATE FOR THE PRESERVATION OF WOOD OR WOOD MATERIALS

[75] Inventors: Wolfgang Metzner, Krefeld; Luzian Naczinski, Meerkamp-Lank; Hans-Werner Wegen, Krefeld, all of Fed. Rep. of Germany

[73] Assignee: Desowag Materialschutz GmbH, Duesseldorf, Fed. Rep. of Germany

[21] Appl. No.: 485,890

[22] Filed: Feb. 28, 1990

[30] Foreign Application Priority Data

Mar. 2, 1989 [DE] Fed. Rep. of Germany ....... 3906556

[51] Int. Cl.$^5$ .............................................. A01N 37/34
[52] U.S. Cl. ..................... 252/380; 514/383; 514/521
[58] Field of Search ................. 252/380; 514/383, 521

[56] References Cited

U.S. PATENT DOCUMENTS

| 4,256,754 | 3/1981 | Linhart et al. | 424/269 |
| 4,536,506 | 8/1985 | Marcoux et al. | 514/521 |
| 4,611,009 | 9/1986 | Fuch et al. | 514/521 |
| 4,723,984 | 2/1988 | Holmwood et al. | 514/383 |
| 4,734,126 | 3/1988 | Holmwood et al. | 514/383 |
| 4,780,459 | 10/1988 | Matthewson | 514/521 |
| 4,940,729 | 7/1990 | Matthewson | 514/521 |
| 4,975,429 | 12/1990 | Brandes et al. | 514/383 |
| 4,990,527 | 2/1991 | Brandes et al. | 514/383 |

FOREIGN PATENT DOCUMENTS

| 0052424 | 5/1982 | European Pat. Off. . |
| 0254857 | 2/1988 | European Pat. Off. . |
| 0269817 | 6/1988 | European Pat. Off. . |

OTHER PUBLICATIONS

Worthing, Charles R. *The Pesticide Manual* 8th edition, The British Crop Protection Council, 1987 pp. 205-206 and 3640.

*Primary Examiner*—Robert L. Stoll
*Assistant Examiner*—Valerie Fee
*Attorney, Agent, or Firm*—Foley & Lardner

[57] ABSTRACT

The present invention relates to a composition for use as an agent or concentrate for the preservation of wood and wood materials, which comprises 0.05 to 25% by weight of a 1-aryl-3-hydroxy-3-alkyl-4-(1,2,4-triazol-1-yl)-butane derivative and 0.002-5% by weight of a pyrethroid insecticide comprising cyano-(4-fluoro-3-phenoxyphenyl)-methyl 3-(2,2-dichloroethenyl)-2,2-dimethylcyclopropanecarboxylate, (±)α-cyano-3-phenoxybenzyl (±)-cis,trans-3-(2,2-dichlorovinyl)-2,2-dimethylcyclopropanecarboxylate, (S)α-cyano-3-phenoxybenzyl (1R,3R)-3-(2,2-dibromovinyl)-2,2-dimethylcyclopropanecarboxylate or 3-phenoxybenzyl (±)-cis,trans-3-(2,2-di-chlorovinyl)-2,2-dimethylcyclopropanecarboxylate or enantiomeric compounds thereof and more than 40% by weight of a solvent and/or diluent as well as, if appropriate, an organic chemical binder and/or fixing agent, processing aids, dye, pigment, dye mixture or pigment mixture.

22 Claims, No Drawings

COMPOSITION FOR USE AN AN AGENT OR CONCENTRATE FOR THE PRESERVATION OF WOOD OR WOOD MATERIALS

BACKGROUND OF THE INVENTION

The present invention relates to a composition for use as an agent or concentrate for the preservation of wood and wood materials on the basis of or with the additional use of 1-aryl-3-hydroxy-3-alkyl-4-(1,2,4-triazol-1-yl)-butane derivatives of the formula

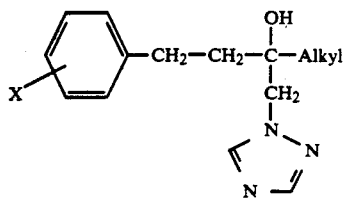

wherein X is halogen, alkylthio having 1 to 4 carbon atoms or halogenoalkoxy having 1 or 2 carbon atoms and 1 to 5 halogen atoms and Alkyl is an alkyl group having 1 to 4 carbon atoms, and/or acid addition salts thereof and metal salt complexes thereof, and at least one solvent, diluent and/or additive.

The said 1-aryl-3-hydroxy-3-alkyl-4-(1,2,4-triazol-1-yl)-butane derivatives are known from German Offenlegungsschrift 3,621,494 and are used as agents having a fungicidal action for the protection of engineering materials from damage or destruction by microorganisms.

Wood preservatives, however, have to meet requirements which go beyond the purely fungicidal activity.

SUMMARY OF THE INVENTION

It is therefore an object of the present invention to provide a wood preservative which is highly active for an extended time period against wood-discoloring and wood-destroying fungi and also against wood-damaging insects, in particular against wood-destroying long-horned beetles (Cerambycidae, Lyctidae, Bostrychidae and Anobiidae) and termites. Another object of the present invention is to provide a wood preservative wherein the activity of the fungicide is not impaired by the insecticide and vice versa. Furthermore, the wood preservative should show good penetrating power in the wood and wood materials.

In accomplishing the foregoing objects, an agent or concentrate for the preservation of wood and wood materials is provided according to the present invention, which comprises: 0.05–25% by weight of a fungicide comprising 1-aryl-3-hydroxy-3-alkyl-4-(1,2,4-triazol-1-yl)-butane derivative of the formula

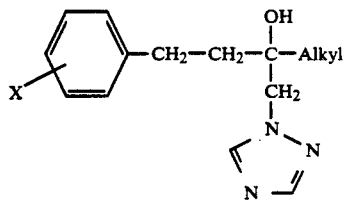

wherein which X is halogen, alkylthio having 1 to 4 carbon atoms or halogenoalkoxy having 1 or 2 carbon atoms and 1 to 5 halogen atoms and Alkyl is an alkyl group having 1 to 4 carbon atoms, or an acid addition salt of the derivative or a metal salt complex of the derivative or a mixture thereof; 0.002–5% by weight of a pyrethroid insecticide comprising cyano-(4-fluoro-3-phenoxyphenyl)-methyl -3-(2,2-dichloroethenyl)-2,2-dimethylcyclopropanecarboxylate, (±)-α-cyano-3-phenoxybenzyl (±)-cis,trans-3-(2,2,-dichlorovinyl)-2,2-dimethylcyclopropanecarboxylate, (S)-α-cyano-3-phenoxybenzyl(1R, 3R)-3-(2,2-dibromovinyl)-2,2-dimethylcyclopropanecarboxylate or 3-phenoxybenzyl (±)-cis,trans-3-(2,2-dichlorovinyl)-2,2-dimethylcyclopropanecarboxylate or enantiomeric compounds thereof; and more than 40% by weight of a mixture comprising at least one constituent selected from the group consisting of a solvent, diluent, organic chemical binder, fixing agent, plasticizer, processing aid, dye, pigment, dye mixture and pigment mixture.

Further objects, features and advantages of the present invention will become apparent from the detailed description of preferred embodiments that follows.

DETAILED DESCRIPTION OF THE PREFERRED EMBODIMENTS

The solvent and/or diluent comprises an organic chemical solvent -or solvent mixture and/or an oily or oil-like organic chemical solvent or solvent mixture of low volatility and/or a polar organic chemical solvent or solvent mixture and/or water and at least one emulsifier and/or wetting agent.

Preferably, the agent or concentrate according to the invention comprises 1-(4-fluorophenyl) -3-hydroxy-3-tert.-butyl-4-(1,2,4triazol-1-yl)-butane, 1-(4-chlorophenyl)-3-hydroxy-3-tert.butyl -4-(1,2,4-triazol-1-yl)-butane or 1-(4-bromophenyl)-3-hydroxy-3-tert.-butyl-4-(1,2,4-triazol-1-yl)-butane as the 1-aryl-3-hydroxy-3-alkyl-4-(1,2,4-triazol-1-yl)-butane derivative.

The organic chemical solvents used are preferably oily or oil-like solvents having an evaporation number above 35 and a flashpoint above 30° C., preferably above 45° C. As such water-insoluble, oily or oil-like solvents of low volatility, appropriate mineral oils or the aromatics fractions thereof or mineral oil-containing solvent mixtures, preferably white spirit, petroleum and/or alkylbenzene, are used.

Advantageously, mineral oils having a boiling range of 170°–220° C., white spirit having a boiling range of 170°–220° C., spindle oil having a boiling range of 250°C.–350° C., petroleum or aromatics of boiling range 160°–280° C., turpentine oil and the like are used.

In a preferred embodiment, liquid aliphatic hydrocarbons having a boiling range of 180°–210° C. or high-boiling mixtures of aromatic and aliphatic hydrocarbons having a boiling range of 180° to about 220° C. and/or spindle oil and/or monochloronaphthalene, preferably a-monocholoronaphthalene, are used.

The organic oily or oil-like solvents of low volatility having a evaporation number above 35 and a flashpoint above 30° C., preferably above 45° C., can be partially replaced by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, a part of the organic chemical solvent or solvent mixture is replaced by an aliphatic polar organic chemical solvent or solvent mixture. Preferably, aliphatic organic chemical solvents such as, for example, glycol ethers, esters or the like, containing hydroxyl groups and/or ester groups and/or ether groups are used.

The organic chemical binders used within the scope of the present invention are the synthetic resins and/or binding drying oils, which are known and are water-dilutable and/or soluble or dispersible and/or emulsifiable in the organic chemical, solvents used, especially binders consisting of or containing an acrylate resin, a vinyl resin, for example polyvinyl acetate, a polyester resin, a polycondensation or polyaddition resin, a polyurethane resin, an alkyd resin or modified alkyd resin, a phenolic resin, a hydrocarbon resin such as indene-/cumarone resin, a silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used up to 10% by weight of the binder. In addition, dyes, pigments, water repellents, odor correctives and inhibitors or anticorrosive agents and the like, which are known, can be used.

According to the present invention, the agent or concentrate preferably includes. as the organic chemical binder, at least one alkyd resin or modified alkyd resin and/or a drying vegetable oil. Preferably, alkyd resins having an oil content of more than 45% by weight, preferably 50 to 68% by weight, are used according to the present invention.

The organic chemical binder or binder mixture can be replaced wholly, preferably partially, by at least one fixing agent or at least one plasticizer.

In this case, from 0 to 75% by weight, preferably from 0.01 to 35% by weight (relative to 100% by weight of binder used, calculated as a solid) of the organic chemical binder or binder mixture is replaced by the same quantities by weight of at least one fixing agent or at least one plasticizer.

Preferably, those compounds are used as the fixing agent or plasticizer which, in addition to certain binding or adhesion to the active compound, also prevent volatilization of the active compounds and/or crystallization or precipitation, such as a) plasticizers, for example, alkyl, aryl or aralkyl phthalates, preferably dibutyl, dioctyl and benzyl butyl phthalates, alkyl phosphates or phosphoric acid esters, preferably tributyl phosphate, adipates, preferably di-(2-ethylhexyl) adipate, stearates and oleates, for example, alkyl stearates or alkyl oleates, preferably butyl oleate, butyl stearate or amyl stearate, bis(dimethylbenzyl) ether, ethyl p-toluenesulfonate, glycerol esters, glycerol ethers or higher-molecular glycol ethers, and/or b) fixing agents based on ketones and/or polyvinyl alkyl ethers, for example, ketones having alkyl, aryl or aralkyl groups, preferably benzophenone and ethylbenzophenone, or polyvinyl ethers, preferably polyvinyl methyl ether.

According to a preferred embodiment, a ready-to-use agent comprises 0.2 to 3% by weight, preferably 0.5 to 2% by weight, of the 1-aryl-3-hydroxy-3-alkyl-4-(1,2,4-triazol-1-yl)-butane derivative, 0.005 to 1% by weight, preferably 0.01 to 0.5% by weight, of the pyrethroid insecticide and at least one organic chemical solvent or solvent mixture and/or an oily or oil-like organic chemical solvent or solvent mixture of low volatility and/or a polar organic chemical solvent or solvent mixture and/or water and an emulsifier and/or wetting agent and, if appropriate, 0 to 5% by weight, preferably 0.1 to 3% by weight, of fixing agent and/or other additives as the remaining constituent.

According to another preferred embodiment, the ready-to-use agent comprises 0.2 to 3% by weight, preferably 0.5 to 2% by weight, of the 1-aryl-3-hydroxy-3-alkyl-4-(1,2,4-triazol-1-yl) -butane derivative, 0.005 to 1% by weight, preferably 0.01 to 0.5% by weight, of the pyrethroid insecticide, 2 to 30% by weight, preferably 5 to 22% by weight, calculated as a solid, of a synthetic resin binder, preferably an alkyd resin and/or a drying vegetable oil, as well as, at least one organic chemical solvent or solvent mixture and/or an oily or oil-like organic chemical solvent or solvent mixture of low volatility and/or a polar organic chemical solvent or solvent mixture and/or water and an emulsifier and/or wetting agent, as well as, if appropriate, siccatives, dyes, colored pigments and/or UV stabilizers as the remaining constituent.

A concentrate according to the present invention for the preservation of wood and wood materials comprises, according to a preferred embodiment, 0.2 to 25% by weight, preferably 3 to 8% by weight, of the 1-aryl-3-hydroxy-3-alkyl-4-(1,2,4-triazol-1-yl)-butane derivative, 0.05 to 5% by weight, preferably 0.5 to 1% by weight, of the pyrethroid insecticide and 5 to 40% by weight, preferably 10 to 30% by weight, (calculated as a solid) of at least one organic chemical binder and/or fixing agent or plasticizer as well as, an organic chemical solvent or solvent mixture and/or an oily or oil-like organic chemical solvent or solvent mixture of low volatility and/or a polar organic chemical solvent or solvent mixture and/or a penetration aid and/or water and an emulsifier and/or wetting agent as the remaining constituent.

According to one embodiment, the agent or concentrate includes, as an emulsifier or emulsifier mixture, at least one ethoxylated phenol having a side group, preferably an ethoxylated nonylphenol, and/or an ethoxylated fatty acid.

According to another embodiment, the concentrate and the agent prepared therefrom for the preservation of wood and wood materials includes a mixture of emulsifiers of different chain lengths, of which at least one emulsifier has an ethoxylated side chain of less than 10 ethoxy groups and of which at least one other emulsifier has an ethoxylated side chain of more than 10 ethoxy groups.

Advantageously, the concentrate and the agent include, as the water-dilutable synthetic resin, an alkyd resin which has a medium oil length. The result of the use of this synthetic resin is that, in spite of the small proportion of the organic chemical solvent, for example, based on petroleum, better fixing of the active compounds is obtained on the one hand and, depending on the proportion of synthetic resin, film formation is made possible on the other hand.

According to an advantageous embodiment, 0 to 50% by weight, preferably 0.5 to 25% by weight, of the 1-aryl-3-hydroxy-3-alkyl-4-(1,2,4-triazol-1-yl)-butane derivative (relative to 100% by weight of 1-aryl-3-hydroxy-3-alkyl-4-(1,2,4-triazol-1-yl) -butane derivative used) is replaced in the agent or concentrate according to the present invention by the same quantity by weight of another fungicide, preferably N-dichlorofluoromethylthio-N',N'-dimethyl-N-phenylsulfamide (dichlofluanid) and/or N -(dichlorofluoromethylthio)-N',N'- dimethyl-N-p -tolylsulfamide (methyleuparen) and/or 1-[[2-(2,4 -dichlorophenyl)-1,3-dioxolan-2-yl]-methyl]-1H -1,2,4-triazole (azaconazol) and/or 1-[[2-(2,4-dichlorophenyl)-4-propyl-1,3-dioxolan-2-yl]-methyl]-1H-1,2,4-triazole (propiconazol) and/or tributyltin naphthenate and/or methyl benzimidazol-2-yl-carbamate (carbendazim). The latter compound is used in particular in aqueous formulations.

In the agent or concentrate according to the present invention, the cyano-(4-fluoro-3-phenoxyphenyl) -methyl 3-(2,2-dichloroethenyl)-2,2-dimethylcyclopropanecarboxylate, (±)α-cyano-3-phenoxybenzyl (±)-cis,trans-3-(2,2-dichlorovinyl) -2,2-dimethylcyclopentanecarboxylate, (S)α-cyano-3-phenoxybenzyl (1R,3R)-3-(2,2-dibromovinyl)-2,2-dimethylcyclopropanecarboxylate or 3-phenoxybenzyl (±) cis,trans-3- (2,2-dichlorovinyl) -2,2-dimethylcyclopropanecarboxylate or enantiomeric compounds thereof can, depending on the intended use, advantageously be partially replaced by another pyrethroid, an insecticidal carbamate or an insecticidal phosphate, thiophosphate, dithiophosphate or thionophosphate ester.

According to a preferred embodiment, the agent or concentrate according to the present invention is substantially free of aromatic hydroxy alcohols.

The agent or concentrate according to the present invention for the preservation of wood and wood materials is employed against the following wood-destroying insects and wood-destroying fungi:

A. Wood-destroying insects such as:

A.1. Beetles

*Hylotrupes bajulus, Chlorophorus pilosus, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthea rugicollis, Xyleborus spec., Tryptodendron spec., Apate monachus, Bostrychus capucins, Heterobostrychus brunneus, Sinoxylon spec, Dinoderus minutus.*

A.2. Hymenoptera

*Sirex juvencus, Urocerus gigas, Urocerus gigas taignus, Urocerus augur.*

A.3. Termites

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

B. Wood-destroying fungi such as:

B.1. Basidiomycetes

*Coniophora puteana, Coriolus versicolor,*

Poria placenta, Poria monticola, Poria vaporaria, Poria vaillantii, Gloeophyllum sepiarium, Gloeophyllum adoratum, Gloeophyllum abietinum, Gloeophyllum trabeum, Gloephyllum protactum, Lentinus lepideus, Lentinus edodes, Lentinus cyathiformes, Lentinus squarrolosus, Paxillus panuoides, Tyromyces palustris, Pleurotus ostreatus, Donkioporiaexpansa, Serpula lacrymans, Serpula himantoides, Glenospora graphii.

B.2. Deuteromycetes

*Cladosporium herbarum.*

B.3. Ascomycetes

*Chaetomium globosum, Chaetomium albaarenulum, Petriella setifera, Trichurus spiralis, Humicola grisea.*

C. Wood-discoloring fungi such as:

C.1. Deuteromycetes

*Aureobasidium pullulans, Sclerophoma pithyophila, Scopularia phycomyces, Aspergillus niger, Penicillium variabile, Trichoderma viride, Trichoderma lignorum, Dactyleum fusarioides.*

C.2. Ascomycetes

*Caratocystis minor.*

C.3. Zygomycetes

*Mucor spinosus.*

Insecticidal test

Testing of the preventive action against recently hatched larvae of the house longhorn beetle (*Hylotrupes bajulus*) after wind tunnel treatment and planing a 2 mm, 3 mm and 4 mm layer off from the treated wood surfaces.

The test was carried out partially in accordance with DIN EN 46.

Wood preservatives according to the invention:

| | |
|---|---|
| 1-(4-Chlorophenyl)-3-hydroxy-3-tert.-butyl-4-(1,2,4-triazol-1-yl)-butane | 1.50% |
| Cyano-(4-fluoro-3-phenoxyphenyl)-methyl 3-(2,2-dichloroethenyl)-2,2-dimethyl-cyclopropanecarboxylate (cyfluthrin) | 0.05% |
| Butyldiglycol | 3.00% |
| Methoxypropyl acetate | 1.50% |
| Organic chemical solvent (mixture of aliphatic and aromatic hydrocarbons) | 93.575% |
| Dye | 0.375% |

TABLE 1

| Quantity of wood preservation applied per m² of wood surface | Layer planed off (mm) | Test duration in weeks | Number and condition of the test animals | | | |
|---|---|---|---|---|---|---|
| | | | dead | | alive | |
| | | | not burrowed in | burrowed in | burrowed in | not burrowed in |
| 150 g | 2 | 4 | 10 | 0 | 0 | 0 |
| | | | 10 | 0 | 0 | 0 |
| | | | 10 | 0 | 0 | 0 |
| | | | 10 | 0 | 0 | 0 |
| | | | 10 | 0 | 0 | 0 |
| | | | 10 | 0 | 0 | 0 |
| | | | 10 | 0 | 0 | 0 |
| 150 g | 3 | 4 | 10 | 0 | 0 | 0 |
| | | | 10 | 0 | 0 | 0 |
| | | | 10 | 0 | 0 | 0 |
| | | | 10 | 0 | 0 | 0 |
| | | | 10 | 0 | 0 | 0 |
| 150 g | 4 | 4 | 10 | 0 | 0 | 0 |
| | | | 10 | 0 | 0 | 0 |
| | | | 10 | 0 | 0 | 0 |
| | | | 10 | 0 | 0 | 0 |
| untreated control samples | | | 0 | 2 | 7 | 1 |
| | | | 0 | 0 | 9 | 1 |
| | | | 0 | 2 | 7 | 1 |
| | | | 1 | 0 | 7 | 2 |
| | | | 1 | 1 | 7 | 1 |
| | | | 1 | 1 | 8 | 0 |

Fungicidal test

Wood preservative according to the invention as in the insecticidal test.

Determination of the depth of action of the wood preservative against wood-destroying Basidiomycetes after planing off.

The examination of the small wood blocks, painted and planed off before the fungus test, was carried out in accordance with EN 133. The test specimens (small pine blocks of dimensions: 50×25××15 mm) were, after oven-drying and weighing, sealed at the bend-grain faces. The wood preservative was applied in a quantity of 150 g/m: to the small blocks thus prepared.

The small woods were then stored for four weeks in a conditioned chamber at 20° C. air temperature and 65% relative humidity for drying and conditioning. One day before the start of the fungal test, a layer of 1 mm, 2 mm and 3 mm was planed off from all four sides of the specimen woods. The weights of the individual specimen woods were determined before and after planing-off. One day later, two of the planed-off small blocks in each case were installed on pure cultures of two wood-destroying Basidiomycetes (*Coniophora putea* and *Gloeophyllum trabeum*) next to an untreated small comparison block in Kolle dishes and exposed for 16 weeks to the fungus attack.

The following table shows the mean weight loss and the number of attached small blocks.

TABLE 2

| Fungus | Planed-off layer | Weight loss in % | Number of attacked small wood blocks |
|---|---|---|---|
| *Gloeoph. trabeum* | 0 mm | 0.7 | 0 |
|  | 1 mm | 0.7 | 0 |
|  | 2 mm | 1.4 | 0 |
|  | 3 mm | 1.0 | 0 |
| untreated control sample |  | 44.8 | all |
| *Coniophora puteana* | 0 mm | 0.5 | 0 |
|  | 1 mm | 0.9 | 0 |
|  | 2 mm | 0.7 | 0 |
|  | 3 mm | 0.9 | 0 |
| untreated control sample |  | 52.7 | all |

EXAMPLES

1. Varnish-type wood preservative (colorless)

| | |
|---|---|
| 1-(4-Chlorophenyl)-3-hydroxy-3-tert.-butyl-4-(1,2,4-triazol-1-yl)-butane | 1.5% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.01% by weight |
| N-Dichlorofluoromethylthio-N', N'-dimethyl-N-phenylsulfamide (dichlofluanid) | 0.55% by weight |
| Alkyd resin (100%) | 15.0% by weight |
| Siccatives, wetting agent, antisettling agent | 1.0% by weight |
| Butyldiglycol | 3.0% by weight |
| Solvent (mixture of aromatic and aliphatic hydrocarbons) | 78.94% by weight |

2. Varnish-type wood preservative (colored)

| | |
|---|---|
| 1-(4-Chlorophenyl)-3-hydroxy-3-tert.-butyl-4-(1,2,4-triazol-1-yl)-butane | 1.5% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.01% by weight |
| N-Dichlorofluoromethylthio-N',N'-dimethyl-N-phenylsulfamide (dichlofluanid) | 0.55% by weight |
| Alkyd resin (100%) | 23.0% by weight |
| Pigment | 3.0% by weight |
| Siccatives, wetting agent, antisettling agent | 1.0% by weight |
| Butyldiglycol | 3.0% by weight |
| Solvent (mixture of aromatic and aliphatic hydrocarbons) | 67.94% by weight |

3. Wood preservative having a priming action

| | |
|---|---|
| 1-(4-Chlorophenyl)-3-hydroxy-3-tert.-butyl-4-(1,2,4-triazol-1-yl)-butane | 1.5% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.01% by weight |
| N-Dichlorofluoromethylthio-N',N'-dimethyl-N-phenylsulfamide (dichlofluanid) | 0.55% by weight |
| Alkyd resin (100%) | 7.0% by weight |
| Butyldiglycol | 3.0% by weight |
| Siccatives | 0.2% by weight |
| Solvent (mixture of aromatic and aliphatic hydrocarbons) | 87.74% by weight |

4. Wood preservative having a preventive action for timber work (colorless)

| | |
|---|---|
| 1-(4-Chlorophenyl)-3-hydroxy-3-tert.-butyl-4-(1,2,4-triazol-1-yl)-butane | 1.5% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.05% by weight |
| Butyldiglycol | 3.0% by weight |
| Methoxypropyl acetate | 1.5% by weight |
| Solvent (mixture of aromatic and aliphatic hydrocarbons) | 93.95% by weight |

5. Wood preservative having a preventive action for timber work (colored)

| | |
|---|---|
| 1-(4-Chlorophenyl)-3-hydroxy-3-tert.-butyl-4-(1,2,4-triazol-1-yl)-butane | 1.5% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.05% by weight |
| Butyldiglycol | 3.0% by weight |
| Methoxypropyl acetate | 1.5% by weight |
| Dye (fatty brown B) | 0.6% by weight |
| Solvent (mixture of aromatic and aliphatic hydrocarbons) | 93.35% by weight |

6. Wood preservative having a suppressing action

| | |
|---|---|
| 1-(4-Chlorophenyl)-3-hydroxy-3-tert.-butyl-4-(1,2,4-triazol-1-yl)-butane | 2.0% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.1% by weight |
| Butyldiglycol | 2.0% by weight |
| Dibutyl phthalate | 4.0% by weight |
| Solvent (mixture of aromatic and aliphatic hydrocarbons) | 91.9% by weight |

7. Concentrate for the preservation of wood and wood materials

| | |
|---|---|
| 1-(4-Chlorophenyl)-3-hydroxy-3-tert.-butyl-4-(1,2,4-triazol-1-yl)-butane | 2.0% by weight |
| Cyano-(4-fluoro-3-phenoxy-phenyl)-methyl 3-(2,2-dichloroethenyl)-2,2-dimethyl-cyclopropanecarboxylate (cyfluthrin) | 0.15% by weight |
| Butyldiglycol | 2.0% by weight |
| Alkyd resin (100%) | 10.0% by weight |
| Solvent | 85.85% by weight |

-continued

| | | |
|---|---|---|
| (mixture of aromatic and aliphatic hydrocarbons) | | |
| 8. Concentrate for the preservation of wood and wood materials | | |
| 1-(4-Chlorophenyl)-3-hydroxy-3-tert.-butyl-4-(1,2,4-triazol-1-yl)-butane | 8.0% | by weight |
| Cyano-(4-fluoro-3-phenoxy-phenyl)-methyl 3-(2,2-dichloroethenyl)-2,2-dimethyl-cyclopropanecarboxylate (cyfluthrin) | 0.5% | by weight |
| Butyldiglycol | 5.0% | by weight |
| Alkyd resin (100%) | 20.0% | by weight |
| Solvent (mixture of aromatic and aliphatic hydrocarbons) | 66.5% | by weight |
| 9. Concentrate for the preservation of wood and wood materials, water-dilutable | | |
| 1-(4-Chlorophenyl)-3-hydroxy-3-tert.-butyl-4-(1,2,4-triazol-1-yl)-butane | 8.0% | by weight |
| Cyano-(4-fluoro-3-phenoxy-phenyl)-methyl 3-(2,2-dichloroethenyl)-2,2-dimethyl-cyclopropanecarboxylate (cyfluthrin) | 0.5% | by weight |
| Methyl benzimidazol-2-yl-carbamate (carbendazim) | 1.6% | by weight |
| Alkyd resin (100%) | 30.0% | by weight |
| Emulsifier | 10.0% | by weight |
| Water | 49.9% | by weight |
| 10. Varnish-type wood preservative, water-dilutable | | |
| 1-(4-Chlorophenyl)-3-hydroxy-3-tert.-butyl-4-(1,2,4-triazol-1-yl)-butane | 1.5% | by weight |
| Cyano-(4-fluoro-3-phenoxy-phenyl)-methyl 3-(2,2-dichloroethenyl)-2,2-dimethyl-cyclopropanecarboxylate (cyfluthrin) | 0.01% | by weight |
| Methyl benzimidazol-2-yl-carbamate (carbendazim) | 0.3% | by weight |
| Alkyd resin (100%) | 20.0% | by weight |
| Emulsifier | 3.0% | by weight |
| Pigments | 3.0% | by weight |
| Siccatives, wetting agent, antisettling agent | 1.0% | by weight |
| Butyldiglycol | 3.0% | by weight |
| Water | 68.19% | by weight |

What is claimed is:

1. A ready-to-use agent for the preservation of wood and wood materials comprising:
   a) 0.5 to 2% by weight of 1-(4-chlorophenyl) -3-hydroxy-3-tert.butyl-4-(1,2,4-triazol-1-yl)-butane;
   b) 0.005 to 1% by weight of cyano-(4-fluoro -3-phenoxy-phenylmethyl-3-(2,2,-dichlormethanyl0 -2,2-dimethylcyclopropane-carboxylate; and
   c) more than 40% by weight of at least one constituent selected from the group consisting of an organic solvent, water, an emulsifier, a wetting agent, an organic chemical binder, a fixing agent, a penetration aid, a processing aid, a plasticizer, a dye and a pigment.

2. A ready-to-use agent as recited in claim 1, wherein said c) comprises an oily or oil-like organic chemical solvent having low volatility or a polar organic chemical solvent.

3. A ready-to-use agent for the preservation of wood and wood materials as recited in claim 1, wherein said c) comprises at least one constituent selected from the group consisting of an organic chemical solvent, water, an emulsifier and a wetting agent.

4. A ready-to-use agent for the preservation of wood and wood materials as recited in claim 1, comprising 2 to 30% by weight, calculated as a solid, of a synthetic resin binder.

5. A ready-to-use agent for the preservation of wood and wood materials as recited in claim 4, wherein said synthetic resin binder comprises an alkyd resin, drying vegetable oil or a mixture thereof.

6. A ready-to-use agent for the preservation of wood and wood materials as recited in claim 1, wherein 0.5 to 25% by weight of said 1-(4-chlorophenyl)-3-hydroxy-3-tert.butyl-(1,2,4-triazol-1-yl)-butane is replaced by the same quantity by weight of a second fungicide.

7. A composition for use as an agent or concentrate for the preservation of wood and wood materials as recited in claim 6, wherein said second fungicide comprises N-dichlorofluoromethyl-thio-N'-N'-dimethyl -N-phenylsulfamide, N-(dichloro-fluoromethylthio) -N',N'-dimethyl-N-p-tolylsulfamide, 1-[[2-(2,4-dichlorophenyl)-1,3-dioxolan-2-yl]-methyl]-1H-1,2,4-triazole, 1-[[2-(2,4-dichlorophenyl)-4-propyl-1,3-dioxolan-2-yl]-methyl]-1H-1,2,3-triazole, tributyltin naphthenate, methyl benzimidazol-2-yl-carbamate, or a mixture thereof.

8. A ready-to-use agent for the preservation of wood and wood materials as recited in claim 6, wherein said second fungicide is selected from at least one fungicide of the group consisting of N-(dichloro-fluoromethylthio)-N',N'-dimethyl -N-p-tolylsulfamide, 1-((2-(2,4-dichlorophenyl) -1,3-dioxolan-2-yl)-methyl-1H-1,-2,4-triazole, 1-((2-(2,4-dichlorophenyl)-4-propyl-1,3-dioxolan -2-yl)-methyl)-1H-1,2,4-triazole, and tributyltin naphthenate.

9. A ready-to-use agent for the preservation of wood and wood materials as recited in claim 1, wherein said ready-to-use agent is substantially free of aromatic hydroxy alcohols.

10. A ready-to-use agent for the preservation of wood and wood materials as recited in claim 1, wherein said c) comprises an aliphatic polar organic chemical solvent or mixture of such solvents.

11. A ready-to-use agent for the preservation of wood and wood materials as recited in claim 10, wherein said polar organic chemical solvent or solvent mixture comprises an aliphatic organic chemical solvent or solvent mixture, wherein said solvent has at least one of hydroxyl groups, ester groups, or ether groups.

12. A ready-to-use agent for the preservation of wood and wood materials as recited in claim 1, comprising 0.1 to 3% by weight of a fixing agent.

13. A ready-to-use agent for the preservation of wood and wood materials as recited in claim 1, comprising at least one constituent selected from the group consisting of siccatives, dyes, colored pigments, antisetting agents and UV stabilizers.

14. A ready-to-use agent as recited in claim 1, comprising 0.01 to 0.5% of b).

15. A ready-to-use agent as recited in claim 1, wherein c) comprises an organic solvent and at least one of an emulsifier and wetting agent.

16. A ready-to-use agent as recited in claim 15 wherein said organic solvent comprises an oily or oil-like solvent of low volatility.

17. A ready-to-use agent as recited in claim 16, wherein said organic solvent comprises mineral oil or the aromatic fractions thereof.

18. A ready-to-use agent as recited in claim 15 wherein said organic solvent comprises a polar organic solvent.

19. A ready-to-use agent as recited in claim 1, wherein c) comprises an emulsion, dispersion, or solution of a synthetic resin.

20. A ready-to-use agent as recited in claim 1, wherein c) comprises a mixture of aliphatic and aromatic hydrocarbons and optionally an alkyd resin.

21. A ready-to-use agent as recited in claim 1, wherein c) comprises water and optionally an alkyd resin.

22. A ready-to-use agent for the preservation of wood and wood materials consisting essentially of:
   a) 0.5 to 2% by weight of 1-(4-chlorophenyl) -3-hydroxy-3-tert.butyl-4-(1,2,4-triazol-1-yl)-butane;
   b) 0.005 to 1% by weight of cyano-(4-fluoro -3-phenoxy-phenylmethyl-3-(2,2,-dichlormethanyl) -2,2-dimethylcyclopropane-carboxylate; and
   c) more than 40% by weight of at least one constituent selected from the group consisting of an organic solvent, water, an emulsifier, a wetting agent, an organic chemical binder, a fixing agent, a penetration aid, a processing aid, a plasticizer, a dye and a pigment.

* * * * *